(12) United States Patent
Shu et al.

(10) Patent No.: US 6,242,569 B1
(45) Date of Patent: Jun. 5, 2001

(54) REGULATORS OF APOPTOSIS

(75) Inventors: Hong-Bing Shu, South San Francisco; David V. Goeddel, Hillsborough, both of CA (US)

(73) Assignee: Tularik, Inc., South San Francisco, CA (US)

( * ) Notice: Subject to any disclaimer, the term of this patent is extended or adjusted under 35 U.S.C. 154(b) by 0 days.

(21) Appl. No.: 08/795,088

(22) Filed: Feb. 5, 1997

(51) Int. Cl.[7] .................................................... C07K 14/47

(52) U.S. Cl. ..................... 530/350; 530/324; 530/300; 530/329; 435/226

(58) Field of Search ................................... 530/350, 300, 530/324; 435/226

(56) References Cited

U.S. PATENT DOCUMENTS 6,063,760 * 5/2000 Alnemri .................................. 514/2

* cited by examiner

Primary Examiner—Christopher S. F. Low
Assistant Examiner—Gabriele E. Bugaisky
(74) Attorney, Agent, or Firm—Richard Aron Osman

(57) ABSTRACT

The invention provides methods and compositions relating to apopotosis regulating proteins, known as Casper proteins, and related nucleic acids. The proteins may be produced recombinantly from transformed host cells from the disclosed Casper encoding nucleic acid or purified from human cells. The invention provides specific hybridization probes and primers capable of specifically hybridizing with the disclosed Casper gene, Casper-specific binding agents such as specific antibodies, and methods of making and using the subject compositions in diagnosis, therapy and in the biopharmaceutical industry.

8 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 2045 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO:1:

```
GGGACAAAAC TGGAGCTCCA CCGCGGTGGC GGCCGCTCTA GAACTAGTGG ATCCCCCGGG      60

CTGCAGGAAT TCGGCACGAG AGCTTGCAGC CTCACCGACG AGTCTCAACT AAAAGGGACT     120

CCCGGAGCTA GGGGTGGGGA CTCGGCCTCA CACAGTGAGT GCCGGCTATT GGACTTTTGT     180

CCAGTGACAG CTGAGACAAC AAGGACCACG GGAGGAGGTG TAGGAGAGAA GCGCCGCGAA     240

CAGCGATCGC CCAGCACCAA GTCCGCTTCC AGGCTTTCGG TTTCTTTGCC TCCATCTTGG     300

GTGCGCCTTC CCGGCGTCTA GGGGAGCGAA GGCTGAGGTG GCAGCGGCAG GAGAGTCCGG     360

CCGCGACAGG ACGAACTCCC CCACTGGAAA GGATTCTGAA AGAAATGAAG TCAGCCCTCA     420

GAAATGAAGT TGACTGCCTG CTGGCTTTCT GTTGACTGGC CCGGAGCTGT ACTGCAAGAC     480

CCTTGTGAGC TTCCCTAGTC TAAGAGTAGG ATGTCTGCTG AAGTCATCCA TCAGGTTGAA     540

GAAGCACTTG ATACAGATGA GAAGGAGATG CTGCTCTTTT TGTGCCGGGA TGTTGCTATA     600

GATGTGGTTC CACCTAATGT CAGGGACCTT CTGGATATTT TACGGGAAAG AGGTAAGCTG     660

TCTGTCGGGG ACTTGGCTGA ACTGCTCTAC AGAGTGAGGC GATTTGACCT GCTCAAACGT     720

ATCTTGAAGA TGGACAGAAA AGCTGTGGAG ACCCACCTGC TCAGGAACCC TCACCTTGTT     780

TCGGACTATA GAGTGCTGAT GGCAGAGATT GGTGAGGATT TGGATAAATC TGATGTGTCC     840

TCATTAATTT TCCTCATGAA GGATTACATG GGCCGAGGCA AGATAAGCAA GGAGAAGAGT     900

TTCTTGGACC TTGTGGTTGA GTTGGAGAAA CTAAATCTGG TTGCCCCAGA TCAACTGGAT     960

TTATTAGAAA AATGCCTAAA GAACATCCAC AGAATAGACC TGAAGACAAA AATCCAGAAG    1020

TACAAGCAGT CTGTTCAAGG AGCAGGGACA AGTTACAGGA ATGTTCTCCA AGCAGCAATC    1080

CAAAAGAGTC TCAAGGATCC TTCAAATAAC TTCAGGCTCC ATAATGGGAG AAGTAAAGAA    1140

CAAAGACTTA AGGAACAGCT TGGCGCTCAA CAAGAACCAG TGAAGAAATC CATTCAGGAA    1200

TCAGAAGCTT TTTTGCCTCA GAGCATACCT GAAGAGAGAT ACAAGATGAA GAGCAAGCCC    1260

CTAGGAATCT GCCTGATAAT CGATTGCATT GGCAATGAGA CAGAGCTTCT TCGAGACACC    1320

TTCACTTCCC TGGGCTATGA AGTCCAGAAA TTCTTGCATC TCAGTATGCA TGGTATATCC    1380

CAGATTCTTG GCCAATTTGC CTGTATGCCC GAGCACCGAG ACTACGACAG CTTTGTGTGT    1440

GTCCTGGTGA GCCGAGGAGG CTCCCAGAGT GTGTATGGTG TGGATCAGAC TCACTCAGGG    1500

CTCCCCCTGC ATCACATCAG GAGGATGTTC ATGGGAGATT CATGCCCTTA TCTAGCAGGG    1560

AAGCCAAAGA TGTTTTTTAT TCAGAACTAT GTGGTGTCAG AGGGCCAGCT GGAGGACAGC    1620

AGCCTCTTGG AGGTGGATGG GCCAGCGATG AAGAATGTGG AATTCAAGGC TCAGAAGCGA    1680

GGGCTGTGCA CAGTTCACCG AGAAGCTGAC TTCTTCTGGA GCCTGTGTAC TGCGGACATG    1740

TCCCTGCTGG AGCAGTCTCA CAGCTCACCG TCCCTGTACC TGCAGTGCCT CTCCCAGAAA    1800
```

```
CTGAGACAAG AAAGAAAACG CCCACTCCTG GATCTTCACA TTGAACTCAA TGGCTACATG    1860

TATGATTGGA ACAGCAGAGT TTCTGCCAAG GAGAAATATT ATGTCTGGCT GCAGCACACT    1920

CTGAGAAAGA AACTTATCCT CTCCTACACA TAAGAAACCA AAAGGCTGGG CGTAGTGGCT    1980

CACACCTGTA ATCCCAGCAC TTTGGGAGGC CAAGGAGGGC AGATCACTTC AGGTCAGGAG    2040

TTCGA                                                                 2045
```

(2) INFORMATION FOR SEQ ID NO:2:

(i) SEQUENCE CHARACTERISTICS:
        (A) LENGTH: 480 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:2:

```
Met Ser Ala Glu Val Ile His Gln Val Glu Glu Ala Leu Asp Thr Asp
1               5                   10                  15

Glu Lys Glu Met Leu Leu Phe Leu Cys Arg Asp Val Ala Ile Asp Val
            20                  25                  30

Val Pro Pro Asn Val Arg Asp Leu Leu Asp Ile Leu Arg Glu Arg Gly
        35                  40                  45

Lys Leu Ser Val Gly Asp Leu Ala Glu Leu Leu Tyr Arg Val Arg Arg
    50                  55                  60

Phe Asp Leu Leu Lys Arg Ile Leu Lys Met Asp Arg Lys Ala Val Glu
65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Leu His Asn Gly Arg Ser
        195                 200                 205

Lys Glu Gln Arg Leu Lys Glu Gln Leu Gly Ala Gln Gln Glu Pro Val
    210                 215                 220

Lys Lys Ser Ile Gln Glu Ser Glu Ala Phe Leu Pro Gln Ser Ile Pro
225                 230                 235                 240

Glu Glu Arg Tyr Lys Met Lys Ser Lys Pro Leu Gly Ile Cys Leu Ile
                245                 250                 255

Ile Asp Cys Ile Gly Asn Glu Thr Glu Leu Leu Arg Asp Thr Phe Thr
            260                 265                 270

Ser Leu Gly Tyr Glu Val Gln Lys Phe Leu His Leu Ser Met His Gly
        275                 280                 285

Ile Ser Gln Ile Leu Gly Gln Phe Ala Cys Met Pro Glu His Arg Asp
```

-continued

```
                            290                 295                 300
Tyr Asp Ser Phe Val Cys Val Leu Val Ser Arg Gly Gly Ser Gln Ser
305                 310                 315                 320

Val Tyr Gly Val Asp Gln Thr His Ser Gly Leu Pro Leu His His Ile
                325                 330                 335

Arg Arg Met Phe Met Gly Asp Ser Cys Pro Tyr Leu Ala Gly Lys Pro
            340                 345                 350

Lys Met Phe Phe Ile Gln Asn Tyr Val Val Ser Glu Gly Gln Leu Glu
        355                 360                 365

Asp Ser Ser Leu Leu Glu Val Asp Gly Pro Ala Met Lys Asn Val Glu
    370                 375                 380

Phe Lys Ala Gln Lys Arg Gly Leu Cys Thr Val His Arg Glu Ala Asp
385                 390                 395                 400

Phe Phe Trp Ser Leu Cys Thr Ala Asp Met Ser Leu Leu Glu Gln Ser
                405                 410                 415

His Ser Ser Pro Ser Leu Tyr Leu Gln Cys Leu Ser Gln Lys Leu Arg
                420                 425                 430

Gln Glu Arg Lys Arg Pro Leu Leu Asp Leu His Ile Glu Leu Asn Gly
            435                 440                 445

Tyr Met Tyr Asp Trp Asn Ser Arg Val Ser Ala Lys Glu Lys Tyr Tyr
        450                 455                 460

Val Trp Leu Gln His Thr Leu Arg Lys Lys Leu Ile Leu Ser Tyr Thr
465                 470                 475                 480
```

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:3:

```
Gln Ala Cys Arg Gln Gly
1               5
```

REGULATORS OF APOPTOSIS

FIELD OF THE INVENTION

The field of this invention is proteins which regulate cell death.

BACKGROUND

Apoptosis is a cell suicide process of sequential biochemical events triggered by a variety of physiological and stress stimuli. Several lines of evidence indicate that a family of cysteine proteases, or caspases (Alnemri et al., 1996) play a crucial role in execution of apoptosis. Several members of the caspase family have been identified (for review, see Henkart, 1996; for nomenclature, see Alnemri et al., 1996) which share certain characteristic features. For example, all the identified caspases contain a conserved motif QAC(R/Q)G, in which the Cys residue is the structural hallmark of a caspase. This cysteine residue, together with two highly conserved residues, corresponding to His237 and Gly238 in ICE, may form the active site of a caspase (Wilson et al., 1994; Walker et al., 1994). In addition, many members of the family are capable of inducing apoptosis when overexpressed in mammalian cells (Henkart, 1996).

Many divergent stimuli can activate the caspase cascades leading to apoptosis. In recent years, apoptosis induced by TNF and FasL have received extensive attention. TNF elicits a broad range of biological effects (Goeddel, 1986; Beutler and Cerami, 1988; Fiers, 1991) through two distinct membrane receptors, TNF-R1 and TNF-R2, which are expressed at low levels on most cell types (Loetscher et al., 1990; Schall et al., 1990; Smith et al., 1990; Fiers, 1991; Tartaglia and Goeddel, 1992). Apoptosis induced by TNF is mediated primarily through TNF-R1. The intracellular domain of TNF-R1 contains a "death domain" of approximately 80 amino acids that is responsible for signaling cell death by the receptor (Tartaglia et al., 1993). A homologous death domain is also found in the cytoplasmic region of Fas and Wsl/DR3/Apo-3, two other members of the TNF receptor family that can potently induce apoptosis (Itoh and Nagata, 1993; Chinnaiyan et al., 1996b; Kitson et al., 1996; Marsters et al., 1996).

TRADD, a cytoplasmic protein containing a C-terminal death domain, interacts with the death domain of TNF-R1 in a ligand dependent process (Hsu et al., 1995; Hsu et al., 1996a). As observed for TNF-R1, overexpression of TRADD causes both apoptosis and activation of NF-κB (Hsu et al., 1995). The death domain of TRADD also interacts with the cytoplasmic protein FADD (Hsu et al., 1996a) through their respective death domains. Fas and FADD have also been shown to interact directly through their respective death domains (Boldin et al., 1995; Chinnaiyan et al., 1995). Although the death domains of TNF-R1, Fas, and TRADD induce apoptosis following overexpression in mammalian cells (Tartaglia et al., 1993; Hsu et al., 1995; Itoh and Nagata, 1993; Hsu et al., 1996b), overexpression of the C-terminal death domain of FADD inhibits TNF- and Fas-induced cell death (Chinnaiyan et al., 1996a; Hsu et al., 1996a). The N-terminal domain of FADD, termed death effector domain (DED), induces apoptosis after overexpression, suggesting the DED of FADD may activate a downstream cell death signaling component (Chinnaiyan et al., 1996a; Hsu et al., 1996a).

A recently identified a cysteine protease, caspase-8, (previously called Mch5, MACH and FLICE, Fernandes-Alnemri et al., 1996; Boldin et al., 1996; Muzio et al., 1996) may represent the missing link between FADD and the basic cell death machinery. The N-terminal domain of caspase-8 contains two DED-like modules through which it interacts with FADD (Boldin et al., 1996; Muzio et al., 1996). The C-terminal domain of caspase-8 is homologous to members of the caspase family and has protease activity towards most known caspases and PARP (Fernandes-Alnemri et al., 1996; Srinivasula et al., 1996; Muzio et al., 1996). The present invention provides a novel family of proteins termed Casper (csasepase-eight-related protein), which are structurally related to caspase-8.

SUMMARY OF THE INVENTION

The invention provides methods and compositions relating to natural isolated apoptosis regulating proteins called Casper proteins, related nucleic acids, and protein domains thereof having Casper-specific activity. The proteins may be produced recombinantly from transformed host cells from the subject Casper encoding nucleic acids or purified from mammalian cells. The invention provides isolated Casper hybridization probes and primers capable of specifically hybridizing with the disclosed Casper gene, Casper-specific binding agents such as specific antibodies, and methods of making and using the subject compositions in diagnosis (e.g. genetic hybridization screens for Casper transcripts), therapy (e.g. gene therapy to modulate Casper gene expression) and in the biopharmaceutical industry (e.g. as immunogens, reagents for isolating other transcriptional regulators, reagents for screening chemical libraries for lead pharmacological agents, etc.).

DETAILED DESCRIPTION OF THE INVENTION

The nucleotide sequences of a natural cDNA encoding a human Casper protein is shown as SEQ ID NO:1, and the full conceptual translate is shown as SEQ ID NO:2. The Casper proteins of the invention include incomplete translates of SEQ ID NO:1 and deletion mutants of SEQ ID NO:2, which translates and deletion mutants have Casper-specific amino acid sequence and assay-discernable Casper-specific binding specificity or function. Such active Casper deletion mutants, Casper peptides or protein domains comprise at least about 6, preferably at least about 8, more preferably at least about 10 consecutive residues of SEQ ID NO:2. For examples, Casper protein domains identified below are shown to provide protein-binding domains which are identified in and find use, inter alia, in solid-phase binding assays as described below.

Casper-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an Casper protein with a binding target is evaluated. The binding target may be a natural intracellular binding target such as a FADD, TRAF1, TRAF2, Caspase-3 or Caspase-8 protein, or other regulator that directly modulates Casper activity or its localization; or non-natural binding target such a specific immune protein such as an antibody, or an Casper specific agent such as those identified in screening assays such as described below. Casper-binding specificity may assayed by binding equilibrium constants (usually at least about $10^7 M^{-1}$, preferably at least about $10^8 M^{-1}$, more preferably at least about $10^9 M^{-1}$), by the ability of the subject protein to function as negative mutants in Casper-expressing cells, to elicit Casper specific antibody in a heterologous host (e.g a rodent or rabbit), etc. In any event, the Casper binding specificity of the subject Casper proteins necessarily distinguishes Caspase-8 and Mch4.

The claimed Casper proteins are isolated or pure: an "isolated" protein is unaccompanied by at least some of the material with which it is associated in its natural state, preferably constituting at least about 0.5%, and more preferably at least about 5% by weight of the total protein in a given sample and a pure protein constitutes at least about 90%, and preferably at least about 99% by weight of the total protein in a given sample. The Casper proteins and protein domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, N.Y.) or that are otherwise known in the art.

The invention provides natural and non-natural Casper-specific binding agents, methods of identifying and making such agents, and their use in diagnosis, therapy and pharmaceutical development. For example, Casper-specific agents are useful in a variety of diagnostic and therapeutic applications. Novel Casper-specific binding agents include Casper-specific receptors, such as somatically recombined protein receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. For diagnostic uses, the binding agents are frequently labeled, such as with fluorescent, radioactive, chemiluminescent, or other easily detectable molecules, either conjugated directly to the binding agent or conjugated to a probe specific for the binding agent. Agents of particular interest modulate Casper function, e.g. Casper-dependent apoptosis; for example, isolated cells, whole tissues, or individuals may be treated with a Casper binding agent to activate, inhibit, or alter Casper-dependent apoptotic processes.

The amino acid sequences of the disclosed Casper proteins are used to back-translate Casper protein-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural Casper-encoding nucleic acid sequences ("GCG" software, Genetics Computer Group, Inc, Madison Wis.). Casper-encoding nucleic acids used in Casper-expression vectors and incorporated into recombinant host cells, e.g. for expression and screening, transgenic animals, e.g. for functional studies such as the efficacy of candidate drugs for disease associated with Casper-modulated transcription, etc.

The invention also provides nucleic acid hybridization probes and replication/amplification primers having a Casper cDNA specific sequence contained in SEQ ID NO:1 and sufficient to effect specific hybridization thereto (i.e. specifically hybridize with SEQ ID NO:1 in the presence of HeLa cell cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. Casper cDNA homologs can also be distinguished from other protein using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Nucleic acids comprising the nucleotide sequence of SEQ ID NO:1 or fragments thereof, contain such sequence or fragment at a terminus, immediately flanked by a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of Casper genes and gene transcripts and in detecting or amplifying nucleic acids encoding additional Casper homologs and structural analogs. In diagnosis, Casper hybridization probes find use in identifying wild-type and mutant Casper alleles in clinical and laboratory samples. Mutant alleles are used to generate allele-specific oligonucleotide (ASO) probes for high-throughput clinical diagnoses. In therapy, therapeutic Casper nucleic acids are used to modulate cellular expression or intracellular concentration or availability of active Casper. For example, Casper nucleic acids are also used to modulate cellular expression or intracellular concentration or availability of active Casper protein. Casper inhibitory nucleic acids are typically antisense: single-stranded sequences comprising complements of the disclosed natural Casper coding sequences. Antisense modulation of the expression of a given Casper protein may employ antisense nucleic acids operably linked to gene regulatory sequences. Cell are transfected with a vector comprising a Casper sequence with a promoter sequence oriented such that transcription of the gene yields an antisense transcript capable of binding to endogenous Casper encoding MRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given Casper protein may be administered to the target cell, in or temporarily isolated from a host, at a concentration that results in a substantial reduction in expression of the targeted protein. An enhancement in Casper expression is effected by introducing into the targeted cell type Casper nucleic acids which increase the functional expression of the corresponding gene products. Such nucleic acids may be Casper expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of a Casper modulatable cellular function. Generally, these screening methods involve assaying for compounds which modulate Casper interaction with a natural Casper binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Such libraries encompass candidate agents of encompass numerous chemical classes, though typically they are organic compounds; preferably small organic compounds and are obtained from a wide variety of sources including libraries of synthetic or natural compounds. Identified agents find use in the pharmaceutical industries for animal and human trials; for example, the agents may be derivatized and rescreened in in vitro and in vivo assays to optimize activity and minimize toxicity for pharmaceutical development.

In vitro binding assays employ a mixture of components including an Casper protein, which may be part of a fusion product with another peptide or polypeptide, e.g. a tag for detection or anchoring, etc. The assay mixtures comprise a natural intracellular Casper binding target. While native binding targets may be used, it is frequently preferred to use portions (e.g. peptides) thereof so long as the portion provides binding affinity and avidity to the subject Casper protein conveniently measurable in the assay. The assay mixture also comprises a candidate pharmacological agent and typically, a variety of other reagents such as salts, buffers, neutral proteins, e.g. albumin, detergents, protease inhibitors, nuclease inhibitors, antimicrobial agents, etc. The mixture components can be added in any order that provides for the requisite bindings and incubations may be performed at any temperature which facilitates optimal binding. The mixture is then incubated under conditions whereby, but for the presence of the candidate pharmacological agent, the Casper protein specifically binds the cellular binding target, portion or analog with a reference binding affinity. Incubation periods are likewise selected for optimal binding but also minimized to facilitate rapid, high-throughput screening.

After incubation, the agent-biased binding between the Casper protein and one or more binding targets is detected by any convenient way. First, a separation step is generally used to separate bound from unbound components. Separation may be effected by precipitation (e.g. TCA precipitation, immunoprecipitation, etc.), immobilization (e.g on a solid substrate), etc., followed by washing by, for examples, membrane filtration, gel chromatography (e.g. gel filtration, affinity, etc.). One of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the Casper protein to the target in the absence of the agent as compared with the binding affinity in the presence of the agent indicates that the agent modulates the binding of the Casper protein to the Casper binding target. Analogously, in the cell-based transcription assay also described below, a difference in the Casper transcriptional induction in the presence and absence of an agent indicates the agent modulates Casper-induced transcription. A difference, as used herein, is statistically significant and preferably represents at least a 50%, more preferably at least a 90% difference.

The following experimental section and examples are offered by way of illustration and not by way of limitation.

EXPERIMENTAL

Identification of Casper: Although TRADD and FADD interact when overexpressed in yeast and mammalian systems (Hsu et al., 1996a), and a dominant negative mutant of FADD blocks TNF-induced apoptosis (Hsu et al., 1996a; Chinnaiyan et al., 1996a), we have been unable to detect FADD in the endogenous TNF-R1 signaling complex (Shu et al., 1996). This observation implies the possibility that a FADD-like molecule, rather than FADD itself, may be a physiological component of TNF-induced cell death pathway. To identify potential FADD-related genes, we searched a public database of human expressed sequence tags (ESTs). We identified two ESTs (G92, 270 bp and W23795, 313 bp) each capable of encoding a distinct peptide, each of which has approximately 30% sequence identity with the death effector domain (DED) of FADD. Subsequent cDNA cloning and sequence analysis demonstrated that the two ESTs included different fragments of the same gene. The longest cDNA clones obtained had a ~2.1 kb insert (SEQ ID NO:1) and an open reading frame of 480 amino acids (SEQ ID NO:2). We have designed the protein encoded by this cDNA as Casper (for caspase-eight-related protein, see below).

Casper has sequence similarity to the recently cloned caspase-8 throughout its length (Fernades-Alnemri et al., 1996; Boldin et al., 1996; Muzio et al., 1996). It contains two DED-like modules at its N-terminus, each of which shares ~30% sequence identity with the DEDs of FADD, caspase-8 and caspase-10 (Fermandes-Alnemri et al., 1996). The C-terminus contains a domain of ~270 aa with ~25% sequence identity to the C-terminal protease domain of the 479 aa caspase-8. The conserved motifs, QACR(Q)G and HG, which are involved in catalysis and are present in all identified caspases, are not found in Casper. We also obtained two alternatively spliced cDNAs that encode truncated forms of Casper having stop codons after amino acids 202 and 435. Further, Northern blotting analysis indicates that the human Casper gene is expressed as several different transcripts of approximately 1.4, 2.4, 3.8, 6.0 and 9.5 kilobases. These and subsequent data indicate alternative splicing of Casper can be used to regulate apoptosis. Casper's expression is high in skeletal muscle, pancreas, and heart, while undetected in the brain.

Induction of Apoptosis by Casper and Its Protease-like Domain: Since Casper is structurally related to both FADD and caspase-8, we examined whether Casper is involved in signaling pathways leading to apoptosis. Using an established assay (Hsu et al., 1995; 1996a; 1996b), we found that Casper overexpression in HeLa cells induced apoptosis. Analysis of deletion mutants indicated that the protease-like domain of Casper (aa 192–480) was necessary and sufficient to induce apoptosis, and was relatively more potent than full length Casper. This is in contrast to caspase-8, where the full length protein is more potent than its protease domain (aa 217–479) alone at inducing apoptosis. The Casper deletion mutants encoding aa 1–96, aa 192–435, aa 370–480, and the naturally spliced form aa 1–435 did not cause significant cell death in these assays. Interestingly, the naturally spliced variant of Casper, aa 1–202, induced partial apoptosis when overexpressed, similar with that observed for aa 1–198 of caspase-8.

CrmA is a specific caspase inhibitor that can block apoptosis induced by TRADD, FADD, and caspase-8 (Tewari and Dixit, 1995a; Hsu et al., 1995; 1996a). CrmA also protects against Casper-induced apoptosis, indicating that Casper activates a caspase cascade leading to apoptosis.

Although Casper is related to caspase-8 throughout its length, it does not contain the conserved QACR(Q)G SEQ ID NO:3 motif present in all known caspases. The position corresponding to the cysteine-360 in caspase-8 is a tyrosine residue in Casper. To determine whether the tyrosine-360 is involved in cell killing by Casper, we mutated this residue to phenylalanine in Casper (192–480), the Casper derivative that is a potent activator of apoptosis when overexpressed. We found that Casper (192–480Y/F) had significantly weaker apoptotic activity compared to its wild-type counterpart. Therefore, tyrosine 360 of Casper might be a structurally important residue for the apoptosis-inducing activity of Casper.

A Deletion Mutant of Casper Blocks TNF- and Fas-Induced Apoptosis: Full length Casper can induce apoptosis in mammalian cells, whereas Casper (1–435) does not. To ask whether Casper might be involved in Fas or TNF signaling, we determined the effect of Casper (1–435) on TNF- and Fas-mediated apoptosis. When Casper (1–435) was expressed in HeLa cells, it behaved as a dominant negative mutant by inhibiting both TNF- and anti-Fas-induced apoptosis.

Since TRADD and FADD are downstream death signaling proteins of TNF-R1 and Fas, we determined whether Casper (1–435) could inhibit apoptosis induced by these proteins. Expression vectors for TRADD and FADD were co-transfected with expression vector for Casper (1–435) or control vector. Consistent with its ability to inhibit anti-Fas- and TNF-induced apoptosis, Casper (1–435) potently inhibited FADD- and TRADD-induced apoptosis. In parallel experiments, a similar deletion mutant (aa 1–436) of caspase-8 also functioned as an inhibitor of FADD- and TRADD-induced apoptosis . These data implicate Casper in the TNF- and Fas-induced cell death pathways that functions downstream of the death domain containing proteins.

Casper Interacts with Distinct Signaling Proteins: To help elucidate the signaling pathway(s) involving Casper, we searched for Casper-interacting proteins using the yeast two-hybrid system. Several proteins were identified that specifically interacted with Casper, including FADD, caspase-8, caspase-10, TRAF1 and TRAF2. Each of these interactions were confirmed in mammalian cells (see below).

Casper Interacts with FADD and Is Recruited to Fas: Since Casper and FADD interact in yeast two-hybrid assays, we tested whether they also interact in mammalian cells. Casper or its various deletion mutants were co-expressed with FADD in human 293 cells. Co-immunoprecipitation analysis indicated that Casper and FADD interact comparably to the caspase-8-FADD interaction. The two DED-like modules of Casper were required and sufficient for its interaction with FADD, probably with the DED of FADD as indicated by the yeast two-hybrid assays The protease-ike domain of Casper did not interact with FADD. Interestingly, deletion mutants Casper (1–96) and Casper (78–480) which contain either the first DED or second DED interacted with FADD weakly. Casper does not interact with the death domain proteins TRADD and RIP.

To test whether Casper might be a part of the Fas signaling complex, we transfected 293 cells with expression vectors for Fas, FADD and Casper. Cell extracts were immunoprecipitated with an antibody against the extracellular domain of Fas, and co-immunoprecipitating proteins were detected by immunoblotting analysis. Fas did not directly interact with Casper in this assay. However, Casper could be recruited to Fas when FADD was co-expressed. A parallel experiment confirmed earlier observations (Muzio et al., 1996; Boldin et al., 1996) that caspase-8 is recruited to Fas through FADD.

Casper Interacts with Caspase-8 Through Distinct Domains: To test whether Casper interacts with caspase-8 in mammalian cells, 293 cells were transfected with mammalian expression vectors for Flag-tagged Casper and Myc-tagged caspase-8. Cell lysates were immunoprecipitated with anti-Flag antibody and co-immunoprecipitating proteins were analyzed by immunoblotting with anti-Myc antibody. This analysis showed that Casper interacts with caspase-8. Interestingly, the N-terminal DED modules and the C-terminal protease-like domain of Casper can independently interact with caspase-8. Either Casper's first DED-like module (aa 1–96) or its C-terminal 91 amino acids alone is sufficient to immunoprecipitate caspase-8. These data indicate that Casper and caspase-8 can interact through distinct domains.

Since Casper can form a complex with caspase-8, we asked whether Casper and caspase-8 can act synergistically in inducing apoptosis. To test this, we examined apoptosis-inducing activity by Casper (192–480) and caspase-8 (217–479), separately or together, since these domains are responsible for their respective apoptosis-inducing activity. At all doses tested, equivalent amounts of the two expression plasmids together were more potent in inducing apoptosis than either of them alone. This shows that the protease-like domain of Casper and the protease domain of caspase-8 have enhanced apoptotic activity when co-expressed in HeLa cells.

CrmA Interacts with Caspase-8, but not Casper or Caspase-3: CrmA can block cell death induced by TNF, Fas, and their signaling proteins TRADD and FADD (Tewari et al., 1995a; Enari et al., 1995; Hsu et al., 1995; 1996a; 1996b; Chinnaiyan et al., 1996a). In vitro interactions between CrmA and activated caspase-1 or caspase-3 have also been reported (Komiyama et al., 1994; Tewari et al., 1995). Since apoptosis induced by Casper and caspase-8 is also inhibited by CrmA, we examined whether CrmA interacts with these proteins in mammalian cells. In co-transfection and co-immunoprecipitation experiments, neither Casper nor any of its various deletion mutants interacted with CrmA. Further, caspase-3 did not interact with CrmA in this assay. However, caspase-8 interacted with CrmA. Interestingly, the protease domain of caspase-8 (aa 217–479) interacted with CrmA much weaker than the full length caspase-8. These data indicate that the first target of CrmA in Fas- and TNF-induced apoptosis pathways may be caspase-8, and inhibition of Casper-induced apoptosis by CrmA may be due to inhibition of caspase-8 activation by CrmA.

Casper Indirectly Induces Caspase-3 Activity: It has been proposed that caspase-3 may be a downstream component of the Fas- and TNF-R1-induced apoptosis pathways (Femandes-Alnemri et al., 1994; Tewari et al., 1995b; Enari et at., 1995; 1996; Nagata, 1996). Since Casper may be an upstream component of these pathways, and Casper-induced apoptosis is inhibited by the specific caspase inhibitor CrmA, we next examined whether Casper can activate caspase-3. Since the protease-like domain of Casper induces apoptosis more potently than the full length Casper, and since in vitro translated protease domain of caspase-8, but not full length caspase-8, can enzymatically activate caspase-3 (Fernandes-Alnemri, et al., 1996; Boldin et al., 1996; Srinivasula et al., 1996), we tested whether the protease-like domain of Casper has protease activity towards caspase-3. 293 cells were transfected with expression vectors for Casper (192–480) or caspase-8 (217–479). The transfected cell lysates were mixed with in vitro translated $^{35}$S-labeled caspase-3 precursor. We found that lysates containing either Casper (192–480) or caspase (217–479) could process the caspase-3 precursor to its signature ~20 kDa fragment, indicating that both the protease-like domain of Casper and the protease domain of caspase-8 can induce a signaling pathway leading to caspase-3 activation in mammalian cells.

To test whether the protease-like domain of Casper can directly process caspase-3, in vitro translated Casper (192–480) was mixed with $^{35}$S-labeled caspase-3. In vitro translated Casper (192–480) could not process caspase-3, whereas in vitro translated caspase-8 (217–479) could. Thus, activation of caspase-3 by Casper in mammalian cells is probably indirect, while caspase-8 can directly process caspase-3 to its active form.

Casper Interacts with Caspase-3: To examine how Casper indirectly leads to caspase-3 activation, we tested whether the two proteins could physically interact. Expression vectors for Flag-tagged Casper, its various deletion mutants, caspase-8 or its protease domain (aa 217–479) were co-transfected with an expression vector for caspase-3. Transfected cell lysates were then immunoprecipitated with anti-Flag antibody and co-immunoprecipitating caspase-3 was detected by immunoblotting analysis. Casper interacts strongly with caspase-3 and the protease-like domain of Casper is sufficient for this interaction. Interestingly, Casper (192–480Y/F), which is less potent in inducing apoptosis than its wild type counterpart, also interacts weaker with caspase-3 than its wild type counterpart. In these experiments, caspase-8 or its protease domain did not interact with caspase-3.

Although the protease domain of caspase-8 does not interact with caspase-3, it can form a complex with caspase-3 with the addition of the protease-like domain of Casper. These data indicate that the protease-like domain of Casper can recruit caspase-3 to the protease domain of caspase-8.

Casper Is Proteolyticly Processed in Mammalian Cells: In our various transfection experiments, we found that Casper was proteolyticly processed. When N-terminal Flag-tagged Casper was overexpressed in 293 cells and lysates were analyzed by immunoblotting with anti-Flag antibody, an N-terminal fragment of approximately 43 kDa was observed. The C-terminal fragment(s) was not detectable since it was not epitope tagged. Casper (78–480) and Casper (192–480) were also cleaved and the resulting N-terminal fragments were about 34 kDa and 20 kDa, respectively. To detect the processed C-terminal fragment, we constructed a C-terminally Flag-tagged Casper vector. However, C-terminally tagged Casper was not processed, indicating that a free C-terminus may be required for Casper processing.

Interestingly, Casper (192–480Y/F) was only weakly processed in comparison to Casper (192–480). This is consistent with our earlier observation that Casper (192/480Y/F) has weaker cell killing activity and weaker interaction with caspase-3. Casper (1–435), Casper (192–435), and Casper (370–480), which do not induce apoptosis, were not processed, although aa 1–435 and aa 192–435 contain the putative cleavage site. Taken together, these data argue that the apoptosis inducing activity of Casper and its mutants are related to their ability to be processed.

Since the size of the processed N-terminal fragment of Casper (78–480) was only slightly larger than that of non-processed Casper (192–480), we reasoned that the processing site should occur soon after position 366 (the size difference between aa 78–480 and aa 192–480 is 114 amino acids). In that region, there are two aspartate residues, at position 369 and 376, which we mutated to alanine or asparagine, respectively, in Casper. Transient transfection experiments showed that the D376N mutation abolished the processing activity of Casper, while D369A mutation had no effect, indicating Casper is processed after D376. To determine whether the processing of Casper is required for its apoptotic activity, we expressed these point mutants in HeLa cells. Both mutants potently induced cell death, demonstrating that the processing of Casper is not required for its cell killing activity.

Casper Interacts with TRAF1 and TRAF2: In yeast two-hybrid screening experiments using aa 19–2480 (the protease-like domain) of Casper as bait, we identified both TRAF1 and TRAF2 (see above), signaling proteins previously shown to be associated with signaling complexes for both TNF-R1 and TNF-R2 (Rothe et al., 1994; Hsu et al., 1996a; Shu et al., 1996). To test whether Casper interacts with TRAFs in mammalian cells, 293 cells were transfected with expression vectors for Casper, together with expression vectors for TRAF1, TRAF2, TRAF3 and various TRAF2 deletion mutants. Coimmunoprecipitation experiments showed that Casper interacts specifically with TRAF1 and TRAF2, but not with TRAF3. Furthermore, the TRAF-N domain of TRAF2 was required to bind to Casper. In similar experiments, we found that TRAF1 and TRAF2 interact with the protease-like domain, but not the N-terminal region of Casper.

TRAF2 interacts with several signaling proteins, including members of the TRAF family, c-IAP1, c-IAP2, TRADD, TNF-R2, I-TRAF, and A20 (Hsu et al., 1996a; Rothe et al., 1994; 1995b; 1996; Song et al., 1996). Among these TRAF2 interacting proteins, only c-IAP1 and c-IAP2 interact with the TRAF-N domain of TRAF2, whereas the other proteins Interact with the TRAF-C domain. Since Casper interacts with the TRAF-N domain of TRAF2, we examined whether Casper can compete with c-IAP1 for binding to TRAF2. 293 cells were transfected with 3 mg expression vectors for HA-tagged TRAF2 and Myc-tagged c-IAP 1, together with increased amount of expression vector for Casper. Coimmunoprecipitation analysis showed that binding of c-IAP1 to TRAF2 was diminished by increased amount of Casper. Consistent with this observation, Casper and cLAP-1 do not simultaneously bind to TRAF2 when overexpressed in 293 cells.

Since Casper and TRADD interact with different domains of TRAF2, we examined whether TRADD, TRAF2, and Casper can form a complex. Co-transfection and co-immunoprecipitation experiments indicate TRADD and Casper can not simultaneously bind to TRAF2. Furthermore, we could not detect recruitment of Casper to TNF-R1 complex by addition of TRADD, FADD, and TRAF2, separately or all together.

Reagents and Cell Lines: Recombinant human TNF was provided by Genentech, Inc. The rabbit anti-TNFR-1 and anti-Fas antisera, and the monoclonal antibody against the Myc epitope tag were described previously (Tartaglia et al., 1991; Wong and Goeddel, 1994; Hsu et al., 1995). The rabbit anti-human FADD antibody was provided by V. Dixit. The monoclonal antibodies against the Flag (Kodak International Biotechnologies, Inc.), HA (BABCO), AU1 (BABCO) epitopes, the agonistic monoclonal antibody against Fas (Panvera Corporation), the monoclonal antibody against caspase-3 (Transduction Laboratory, Inc.) were purchased from the indicated manufactures. The human 293 embryonic kidney (R. Tjian), HeLa (Y. Jiang) and its derivative HtTA-1 (H. Bujard) cell lines were obtained from the indicated sources.

cDNA Cloning: We screened human HeLa cDNA library with two probes corresponding to the two ESTs (GeneBank accession numbers: W23795 and T30922). For each probe, two partial complementary oligos were synthesized, annealed, and filled in by a Klenow reaction with cold dGTP/dTTP and a-$^{32}$P-dCTP/dATP. cDNA library screening with these two probes was performed following standard procedures (Sambrook, et. al., 1989). A total of 7 independent positive clones were obtained from HeLa cDNA library screening. Further screening of a human umbilical vein endothelial cell (HUVEC) cDNA library in IZAP was performed with the ~0.7 kb Hind IIIU/Ssp I fragment from the C-terminus of Casper obtained from above HeLa cDNA library screening. This resulted in 3 additional positive clones. The cDNA inserts of the positive phage clones were sequenced with an Applied Biosystems model 373A automated DNA sequencer.

Northern Blot Hybridization: Human multiple tissue Northern blots (Clontech) were hybridized under high-stringency conditions using radiolabeled Casper-encoding cDNA probe according to the instructions of the manufacturer.

Mammalian Expression Vectors: Mammalian expression vectors encoding TNF-R1, Flag-tagged TRADD and FADD, Myc-tagged TRADD and RIP, CrmA, pRK5 control vector, and pCMV-b-gal were described previously (Hsu et al., 1995; Hsu et al., 1996a; Hsu et al., 1996b). The expression vector for Fas and AU 1-tagged FADD were provided by V. Dixit. pRK7-caspase-3, pRK7-Flag-caspase-3, and pRK7-Myc-caspase-3: caspase-3 full length cDNA was amplified from Jurkat cDNA library by PCR and the resulting cDNA was inserted into the pRK7 vector (for pRK7-caspase-3), or the pRK7-Flag vector (for pRK7-Flag-caspase-3). pRK7-Myc-caspase-3 was constructed by replacing the Flag epitope with the Myc epitope. pRK7-Myc-CrmA: DNA encoding the Myc epitope was fused in-frame to the 5' of CrmA cDNA in the pRK5-CrmA vector (Hsu et al., 1995) to give pRK7-Myc-CrmA vector. pRK7-Flag-Casper, pRK7-Flag-Casper (1–435), pRK7-Flag-Casper (1–195), pRK7-Flag-Casper (1–96), pRK7-Flag-Casper (78–480), pRK7-Flag-Casper (192–480), and pRK7-Flag-Casper (370–480): PCR fragments encoding corresponding Casper amino acid sequences were in-frame inserted into the N-terminal Flag tagged pRK7-Flag vector. pRK7-Flag-Casper (192–435): The Hind III fragment from the pRK7-Casper (1–435) was replaced with the Hind III fragment from the pRK7-Flag-Casper (192–480) vector to give the pRK7-Flag-HB192–435 vector. pRK5-Casper-C-Flag: The C-terminal Flag-tagged Casper expression vector was constructed by in-frame insertion of PCR amplified Casper cDNA (with a stop codon mutation) to pRK5-C-Flag vector. All N-terminal Myc tagged Casper and Casper deletion mutant vectors were generated by replacement of the N-terminal Flag epitope of the respective vectors with DNA encoding the Myc epitope.

Point mutation (Y to F) at position 360 of Casper on pRK7-Casper (192–480) vector was performed with Chameleon site-directed mutagenesis kit (Stratagene). The other point mutation vectors used in this study were made by PCR.

Transfections: The 293, HeLa, and HtTA-1 cell lines were maintained in high glucose Dulbecco's modified Eagle's medium containing 10% fetal calf serum, 100 mg/ml penicillin G and 100 mg/ml streptomycin (GIBCO). For apoptosis assays, ~2×10$^5$ cells/well were seeded on 6-well (35 mm) dishes. For coimmunoprecipitations, ~2×10$^6$ cells/well were seeded on 100 mm plates. Cells were transfected the following day by the standard calcium phosphate precipitation method (Sambrook et al., 1989).

Apoptosis Assays: β-Galactosidase co-transfection assays for determination of cell death were performed as described (Hsu et al., 1995; 1996a; 1996b). Transfected cells were stained with X-gal as previously described (Shu et al., 1995). The number of blue cells from 8 viewing fields of a 35 mm dish was determined by counting. The average number from one representative experiment is shown.

Yeast Two-hybrid Screening: To construct the vectors using as baits, cDNAs for aa 1–215 (the fragment containing the two DED-like modules) and aa 192–480 (the fragment containing the protease-like domain) of Casper were inserted in frame into Gal4 DNA-bind domain vector pPC97 (Rothe et al., 1994) or pGBT9 (Clontech). The murine fetal liver stromal cell cDNA library, human B cell cDNA library (Clontech), human peripheral lymph node cDNA library (Clontech) were obtained from the indicated resources. The isolation of positive clones and subsequent two-hybrid interaction analyses were carried out as described (Rothe et al., 1994; Hsu et al., 1995; 1996a; 1996b).

Coimmunoprecipitation and Western Analysis: Transfected 293 cells from each 100 mm dish were lysed in 1 ml lysis buffer (20 mM Tris [pH 7.5], 150 mM NaCl, 1% Triton, 1 mM EDTA, 10 μg/ml aprotinin, 10 μg/ml leupeptin, 1 mM PMSF). For each immunoprecipitation, 0.8 ml aliquots of lysates were incubated with 1 μl polyclonal anti-Fas or anti-TNF-R1, or 0.5 μg monoclonal antibody against the epitope tag, and 25 μl of a 1:1 slurry of GammaBind G Plus Sepharose (Pharmacia) for at least one hour. The sepharose beads were washed three times with 1 ml lysis buffer containing 500 mM NaCl. The precipitates were fractionated on SDS-PAGE and subsequent western blotting analyses were performed as described (Hsu et al., 1995).

Assay for Protease Activity: In vitro transcription and translation was performed with the TNT SP6 Coupled Reticulocyte Lysate System (Promega) following manufacture's recommendation. In vitro translated $^{35}$-S labeled Flag-tagged caspase-3 precursor was purified by immunoprecipitation with anti-Flag antibody. The purified caspase-3 precursor was aliquoted and mixed with 10 ml non-labeled in vitro translation product or 10 ml transfected cell lysates from pRK7 control vector, pRK7-Casper (192–480), or pRK7-caspase-8 (217–479). The mixture was buffered with 25 mM HEPES (pH7.5), 0.1% CHAPS, 5 mM EDTA, and 10 mM DTT, and incubated at 30° C. for 1.5 hours. Following incubation, the samples were subjected to SDS-PAGE and autoradiography analysis.

References

Alnemri, E. S., et al. (1996) Cell 87, 171
Beutler, B. and Cerami, A. (1988) Annu. Rev. Biochem. 57, 505–518.
Boldin, M. P., et al. (1995) J. Biol. Chem. 270, 387–391.
Boldin, M. P., Goncharov, T. M., Goltsev, Y. V., and Wallach, D. (1996) Cell 85, 803–815.

Chinnaiyan, A. M., O'Rourke, K., Tewari, M., and Dixit, V. M. (1995) Cell 81, 505–512.
Chinnaiyan, A. M., Tepper, C. G., Seldin, M. F., O'Rourke, K., Kischkel, F.C., Hellbardt, S., Krammer, P. H., Peter, M. E., and Dixit, V. M. (1996a) J. Biol. Chem. 271,4961–4965.
Chinnaiyan, A. M., et al. (1996b) Science 274: 990–992.
Ellis, H. and Horvitz, H. R. (1986) Cell 44:817–829.
Enari, M., Hug, H., Nagata, S. (1995) Nature 375, 78–81.
Enari, M., Talanian, R. V., Wong, W. W. and Nagata, S. (1996) Nature 380, 723–726.
Fermandes-Alnenri, T., et al. (1996) Proc. Natl. Acad. Sci. U.S.A. 93, 7464–7469.
Fiers, W. (1991) FEBS Lett. 285, 199–212.
Fraser, A., and Evan, G. (1996). A license to kill. Cell 85, 781–784.
Goeddel, D. V., Aggarwal, B. B., Gray, P. W., Leung, D. W., Nedwin, G. E., Palladino, M. A., Patton, J. S., et al. (1986) In: *Cold Spring Harbor Symposia on Quantitative Biology*, Vol. 51, Cold Spring Harbor Laboratory Press, Cold Spring Harbor, N.Y., pp. 597–609.
Henkart, P. A. (1996). Immunity 4, 195–201.
Hsu, H., Xiong, J. and Goeddel, D. V. (1995). Cell 81,495–504.
Hsu, H., Shu, H. B., Pan, M. G. and Goeddel, D. V. (1996a). Cell 84, 299–308.
Hsu, H., Huang, J., Shu, H. B., Baichwal, V. and Goeddel, D. V. (1996b) Inmunity 4, 387–396.
Itoh, N. and Nagata,S. (1993) J. Biol. Chem.268, 10932–10937.
Kitson, J., et al. (1996) Nature 384, 372–375.
Komiyama, T., et al. (1994). Proc. Natl. Acad. Sci. USA. 269, 19331–19337.
Loetscher, H., et al. (1990).Cell 61, 351–359.
Martin, S. J., and Green, D. R. (1995) Cell 82, 349–352.
Marsters, S. A., et al. (1996). Current Biology 6:1669–1676.
Miura, M., Zhu, H., Rotello, R., Hartwieg, E. A., and Yuan, J. (1993) Cell 75, 653–660.
Muzio, M., et al. (1996). Cell 85, 817–827.
Nagata, S. (1996). Current Biology 6, 1241–1243.
Ray, C. A., et al. (1992). Cell 69, 597–604.
Rothe, M., Wong, S. C., Henzel, W. J., and Goeddel, D. V. (1994) Cell 78, 681–692.
Rothe, M., et al. (1995). Cell 83, 1243–1253.
Sambrook, J., Fritch, E. F. and Maniatis, T. (1989). *Molecular Cloning: A laboratory Manual*, Second Edition (Cold Spring Harbor, N.Y.: Cold Spring Harbor Laboratory Press).
Schall, T. J., et al. (1990) Cell 61, 361–370.
Shu, H. B., Li, Z., Palacios, M. J., Li, Q. and Joshi, H. C. (1995) J. Cell Sci. 108, 2955–2962.
Shu, H. B., et al. (1996) Proc. Natl. Acad. Sci. USA. 93, 13973–13978.
Smith, C. A., et al. (1990). Science 248, 1019–1023.
Srinivasula, S. M., et al. (1996) Proc. Natl. Acad. Sci. USA 93: 14486–14491.
Tartaglia, L. A., et al. (1991). Proc. Natl. Acad. Sci. USA 88, 9292–9296.
Tartaglia, L. A. and Goeddel, D. V. (1992). Immunol Today13, 151–153.
Tartaglia, L. A., Ayres, T. M., Wong, G. H. W. and Goeddel, D. V. (1993).Cell 74, 845–853.
Tewari, M., and Dixit, V. M. (1995a) J. Biol. Chem. 270, 3255–3260.
Tewari, M., et al. (1995b) Cell 81, 801–809.
Walker, N. P. C., et al. (1994) Cell 78, 343–352.
Wilson, K. P., et al. (1994). Nature 370, 270–274.
Wong, G. H. W., and Goeddel, D. V. (1994) J. Immunol. 152, 1751–1755.
Yuan, J., Shaham, S., Ledoux, S., Ellis, H. M., and Horvitz, H. R. (1993) Cell 75, 641–652.

EXAMPLES

1. Protocol for high throughput Casper1-TRAF1 heterodimer formation assay.

A. Reagents:

Neutralite Avidin: 20 $\mu$g/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.

$^{33}$P Casper protein 10×stock: $10^{-8}$–$10^{-6}$M "cold" Casper supplemented with 200,000–250,000 cpm of labeled Casperl (Beckman counter). P1 ace in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM $NaVo_3$ (Sigma #S-6508) in 10 ml of PBS.

TRAF1: $10^{-7}$–$10^{-5}$M biotinylated TRAF1 in PBS.

B. Preparation of assay plates:

Coat with 120 $\mu$l of stock N-Avidin per well overnight at 4° C.

Wash 2 times with 200 $\mu$l PBS.

Block with 150 $\mu$l of blocking buffer.

Wash 2 times with 200 $\mu$l PBS.

C. Assay:

Add 40 $\mu$l assay buffer/well.

Add 10 $\mu$l compound or extract.

Add 10 $\mu$l $^{33}$P-Casper (20–25,000 cpm/0.1–10 pmoles/well=$10^{-9}$–$10^{-7}$M final conc).

Shake at 25° C. for 15 minutes.

Incubate additional 45 minutes at 25° C.

Add 40 $\mu$M biotinylated TRAF1 (0.1–10 pmoles/40 $\mu$l in assay buffer)

Incubate 1 hour at room temperature.

Stop the reaction by washing 4 times with 200 $\mu$M PBS.

Add 150 $\mu$M scintillation cocktail.

Count in Topcount.

D. Controls for all assays (located on each plate):

a. Non-specific binding b. Soluble (non-biotinylated TRAF1) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated Casper protein comprising SEQ ID NO: 2 or a fragment thereof comprising SEQ ID NO:2, residues 1–96, 1–202, 1–435, 78–480, 192–435, 192–480, 390–480 or residue 360 (tyrosine 360) joined directly to at least 6 residues of SEQ ID NO:2 flanking said tyrosine 360.

2. An isolated protein according to claim 1, wherein said protein specifically binds at least one of a FADD, TRAF1, TRAF2, Caspase-3 or Caspase-8 protein.

3. An isolated protein according to claim 1, wherein said protein comprises SEQ ID NO:2, residues 1–96, 1–202, 1–435, 78–480, 192–435, 192–480 or 390–480.

4. An isolated protein according to claim 1, wherein said protein comprises SEQ ID NO:2, residue 360 (tyrosine 360) joined directly to at least 6 residues of SEQ ID NO:2 flanking said tyrosine 360.

5. An isolated Casper protein made by the method comprising steps: introducing a nucleic acid encoding a Casper protein comprising SEQ ID NO: 2 or a fragment thereof comprising SEQ ID NO:2, residues 1–96, 1–202, 1–435, 78–480, 192–435, 192–480, 390–480 or SEQ ID NO:2, residue 360 (tyrosine 360) joined directly to at least 6 residues of SEQ ID NO:2 flanking said tyrosine 360 into a host cell or cellular extract, incubating said host cell or extract under conditions whereby said nucleic acid is expressed as a transcript and said transcript is expressed as a translation product comprising said protein, and isolating said translation product.

6. An isolated Casper protein according to claim 1, comprising SEQ ID NO:2, residues 1–96.

7. An isolated Casper protein according to claim 1, comprising SEQ ID NO:2, residues 192–435.

8. An isolated Casper protein according to claim 1, comprising SEQ ID NO:2, residues 390–480.

\* \* \* \* \*

UNITED STATES PATENT AND TRADEMARK OFFICE
CERTIFICATE OF CORRECTION

PATENT NO. : 6,242,569 B1  Page 1 of 1
DATED : June 5, 2001
INVENTOR(S) : Hong-Bing Shu et al.

It is certified that error appears in the above-identified patent and that said Letters Patent is hereby corrected as shown below:

<u>Column 20,</u>
After line 61, add claim 9 to read:

-- 9. An isolated protein according to claim 1, wherein said protein comprises SEQ ID NO:2, residue 360 (tyrosine 360) joined directly to at least six residues of SEQ ID NO:2 flanking said tyrosine 360, wherein three of said six residues are located on each side of said tyrosine 360. --

Signed and Sealed this

Eighteenth Day of June, 2002

*Attest:*

JAMES E. ROGAN
*Attesting Officer*  *Director of the United States Patent and Trademark Office*